United States Patent [19]
Sudo et al.

[11] Patent Number: 5,288,560
[45] Date of Patent: Feb. 22, 1994

[54] LAMINATED SANITARY RUBBER ARTICLE

[75] Inventors: Morihiro Sudo, Sumida; Tomoyasu Muraki, Abiko; Eiji Kawachi, Kiryu; Yasushi Kawachi, Ashikaga, all of Japan

[73] Assignee: Daikyo Gomu Seiko, Ltd., Tokyo, Japan

[21] Appl. No.: 827,116

[22] Filed: Jan. 28, 1992

[30] Foreign Application Priority Data

Jan. 30, 1991 [JP] Japan ................... 2-027657
Dec. 19, 1991 [JP] Japan ................... 2-336690

[51] Int. Cl.⁵ ............. B32B 25/08; B65D 39/00; C08L 23/22
[52] U.S. Cl. .................... 428/494; 428/519; 428/520; 428/521; 215/364; 220/DIG. 19; 220/307
[58] Field of Search ............ 428/494, 519, 520, 521; 215/364; 220/DIG. 19

[56] References Cited

U.S. PATENT DOCUMENTS

| 4,316,941 | 2/1982 | Eguchi et al. | 428/421 |
| 4,321,306 | 3/1982 | Eguchi | 428/421 |
| 4,808,453 | 2/1989 | Romberg et al. | 428/494 |
| 4,973,504 | 11/1990 | Ramberg et al. | 428/494 |

Primary Examiner—P. C. Sluby
Attorney, Agent, or Firm—Wenderoth, Lind & Ponack

[57] ABSTRACT

The present invention provides sanitary laminated rubber articles suitable for use as various articles with safety and sanitary property, for example, containers for foods or pharmaceutical chemicals, transporters, instruments, packaging materials and the like. In this sanitary laminated article, the rubber surface is laminated with a resin film comprising a cyclic olefinic compound or bridged polycyclic hydrocarbon compound as a polymeric component.

7 Claims, 3 Drawing Sheets

LAMINATED SANITARY RUBBER ARTICLE

BACKGROUND OF THE INVENTION

1. Field of the Invention

This invention relates to sanitary laminated rubber articles suitable for use as various articles with safety and sanitary property, for example, containers for foods or pharmaceutical chemicals, transporters, instruments, packaging materials and the like.

The rubber article of the present invention has very excellent properties which can be adapted to the standard test values of various official documents, required in this field, and can further satisfy the test items having lately become an important problem from the pharmaceutical standpoint and has good economical property.

2. Description of the Prior Art

As a law concerning packaging materials or instruments of food containers, there is the Food Sanitation Act, providing nonpoisonous property, tasteless property and oderless property. This sanitary property includes heat resistance and hot water resistance. The details thereof are shown in Official Notification No. 370 (December, 1962) and Official Notification No. 20 (April, 1982) of the Ministry of Health and Welfare.

High grade sanitary property and safety are required of containers for pharmaceutical chemicals from the standpoint of influences on the human body. To this end, various test methods or quality standards are provided in, for example, "11th Revision, Japanese Pharmacopoeia" (hereinafter referred to as JP 11), International Standards Organization (ISO), European Pharmacopoeia (EP) U.S. Pharmacopoeia XXI (USP), West Germany Industrial Standard DIN 58, 366–58, 368 (DIN), British Standard 3263 (BS), etc. Furthermore, test items and higher standards from medical standpoint have lately been taken into additional consideration.

As to articles for medical treatment, test methods and quality standards are provided in Official Notification Nos. 300 and 301 (standards for blood-collecting equippments and blood-transfusion sets) of the Ministry of Health and Welfare and Official Notification Nos. 442 and 413 (standards for injection cylinders) of the Ministry of Health and Welfare.

For the above described official documents are useful rubbers such as isoprene rubber (hereinafter referred to as IR), butadiene rubber (BR), ethylene-propylene rubber (EPM), ethylene-propylene-terpolymer (EPDM), isobutylene-isoprene rubber (IIR) or chlorinated rubber of IIR (CIIR) or brominated rubber of IIR (BIIR), isobutylene-isoprene-divinylbenzene terpolymer (DIIR) and the like.

As to rubber articles for foods, various techniques have been developed so as to satisfy the standards or requirements for such use, for example, a method of increasing heat resistance by mixing styrene-isoprene copolymer and polyethylene (Japanese Patent Laid-Open Publication Nos. 76939/1973 and 76940/1973); a method comprising adding tocophenol to EPDM and obtaining a laminated article for packaging a heated and sterilized food (Japanese Patent Laid-Open Publication No. 134574/1978); a rubber composition for food sanitation comprising EPDM with zinc white, a fatty acid salt of zinc and calcium oxide (Japanese Patent Publication No. 25175/1987); and a method of producing a rubber article for foods.

In the techniques of obtaining rubber articles for pharmaceutical chemicals and medical instruments, there have been proposed a method comprising adding ascorbic acid or its derivative and thus preventing formation of N-nitroso compound (Japanese Patent Publication Nos. 34262/1989 and 53696/1989); a nipple composed of BR, BIIR and natural rubber, crosslinked with an organic peroxide (Japanese Patent Publication Nos. 20650/1989); a rubber stopper comprising IR and finely powdered PE (Japanese Patent Publication Nos. 8789/1970); a rubber article for pharmaceutical chemicals, free from release of a zinc salt (Japanese Patent Publication Nos. 40257/1986) and an improved rubber stopper based on this rubber article (Japanese Patent Publication Nos. 57870/1985); and a rubber article for pharmaceutical chemicals and medical articles, comprising IIR, BII, CIIR and superhigh molecular weight PE (Japanese Patent Publication No. 55666/1989).

Furthermore, as a rubber article for pharmaceutical chemicals and medical instruments, comprising a rubber composition coated with a resin film, there are proposed a technique of laminating a vulcanized rubber with a film of polypropylene (PP) (Utility Model Publication Nos. 5751/1969 and 27753/1969); a stopper wholly coated with a fluoro resin excellent in chemical resistance (Utility Model Publication No. 17831/1970); a rubber stopper covered with a trifluoroethylene resin on a surface in contact with a medical liquor (Utility Model Publication No. 21346/1974); a process for the production of a rubber stopper, in particular, laminated with a fluoro resin film on a surface in contact with a medical liquor (Japanese Patent Publication Nos. 1355/1977, 9119/1979, 53184/1982, Japanese Patent Laid-Open Publication Nos. 272134/1986 and 23961/1990); and a rubber stopper consisting of IIR laminated with a fluoro-resin film (Japanese Patent Publication No. 3104/1988 and Utility Model Laid-Open Publication No. 47850/1980), as well known in the art.

In the known techniques, however many rubber compounding agents are studied, elution products or stripped materials occur from the rubber compounding agents or rubbers and contaminate medical liquors. Thus, it has been taken as a means for preventing an exterior medical liquor from contamination to cover a rubber article with a fluoro resin film or PE or PP resin film. However, such sanitary films of fluoro resins, PE, PP, etc. have low bonding strengths to rubber surfaces and are thus stripped readily. A higher bonding strength can be obtained by subjecting the surface of a film to a surface treatment, e.g. by corona discharge, but this is a high grade technique having an economical problem.

SUMMARY OF THE INVENTION

It is an object of the present invention to provide an improved rubber article coated with a resin film having a high bonding strength in simple manner.

It is another object of the present invention to provide a sanitary rubber article laminated with a sanitary resin film being medically and chemically inert and capable of satisfying the test standards of the various official documents.

It is a further object of the present invention to provide a saniatry rubber article, the surface of which is laminated with a resin film comprising a cyclic olefinic compound or bridged polycyclic hydrocarbon compound as a polymeric component.

These objects can be attained by a sanitary rubber article whose rubber surface is laminated with a resin film comprising a cyclic olefinic compound or bridged polycyclic hydrocarbon compound as a polymeric component.

BRIEF DESCRIPTION OF THE DRAWINGS

The accompanying drawings are to illustrate the principle and the merits of the present invention in detail.

DETAILED DESCRIPTION OF THE INVENTION

Figure 1:
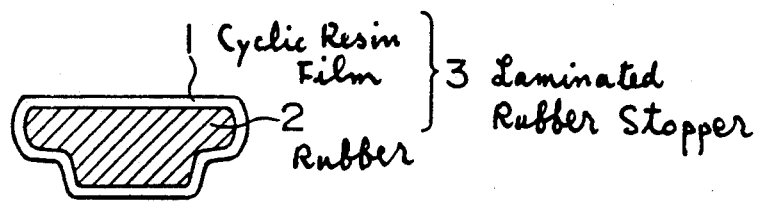
FIG. 1 is a sectional view of one embodiment of the rubber article of the present invention, i.e. the whole surface being laminated with a cyclic resin film of the present invention.

As a means for solving the above described problems, the present invention provides a sanitary rubber article whose rubber surface is laminated with a resin film comprising a cyclic olefinic compound or bridged polycyclic hydrocarbon compound as a polymeric component.

In the present invention, as the above described cyclic olefin compound, monocyclic olefin compounds or alkyl or acrylate derivatives thereof are particularly preferable.

In the present invention, as the above described bridged polycyclic hydrocarbon compound, those containing at least one unsaturated bond in the ring or substituent are particularly preferable.

In the present invention, a resin containing the above described cyclic olefin compound or the above described bridged polycyclic hydrocarbon compound as a polymeric component (which will hereinafter be referred to as "the cyclic resin" of the present invention) includes those containing, as a copolymeric component, lower olefins, aromatic hydrocarbons or aromatic vinyl monomers, and can be mixed with olefin resins.

Furthermore, the cyclic resin of the present invention more preferably has any one of properties, i.e. a bromine number of at most 5 and a softening point of at least 90° C.

Of late, novel and characteristic resin bodies have been developed by a new technique of separating and purifying monomers of $C_5$ fractions obtained by cracking coal tar and naphtha and by a technique relating to catalysts for polymerization of the monomers, and above all, marked progress has been found in polymers of the cyclic olefin monomers, in particular, bridged polycyclic hydrocarbon monomers.

For example, cyclopentadiene obtained from the $C_5$ fractions prepared by cracking naphtha of petroleum fractions is a monomer obtained abundantly with a low cost on a commercial scale. Dimerization of cyclopentadiene (CPD) at room temperature results in dicyclopentadiene (DCP), while thermal cracking of DCP at 140° to 160° C. gives CPD. Using CPD and DCP as a raw material, petroleum resins are produced and applied to production of tackifiers as adhesives in the rubber industry, sizing agent resins for paper making, raw material resins for paints, etc.

Noticing that the resin containing the above described cyclic olefin compound or the above described bridged polycyclic hydrocarbon compound as a polymeric component resin is readily and strongly bonded to the commonly used shaped rubber, the bonded interface being not easily stripped by operations, e.g. steam sterilization, and the resin is inert, very sanitary and non-crystalline, the inventors have found that a rubber article whose surface is laminated with this resin is a very sanitary rubber article capable of passing the test of JP 11, etc. The present invention is based on this finding.

Useful examples of the cyclic resin of the present invention, to be used as a polymeric component, are as follows:

Monocyclic olefin compounds such as,

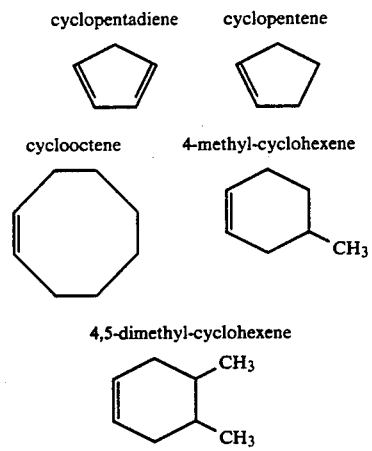

Lower alkyl derivatives of the above described compounds, containing 1 to 3 lower alkyl groups substituted, e.g. methyl group, ethyl group, etc, acrylate derivatives and the like.

As the bridged polycyclic hydrocarbon compound, there are preferably used bridged polycyclic hydrocarbon compounds with two or more rings, in particular, bridged polycyclic olefin compounds or derivatives thereof and bridged polycyclic saturated hydrocarbon compounds having unsaturated bonds in the substituents, i.e. bridged polycyclic cycloalkene compounds and their lower alkyl derivatives, aryl derivatives, aralkyl derivatives, and bridged polycyclic cycloalkane compound vinyl derivatives, allyloxy derivatives, (meth)acryloxy derivatives, etc.

Specifically, the following compounds are given:

bicyclo[2,2,1]-2-heptene,

bicyclo[2,2,1]-2,5-heptadiene (2,5-norbornadiene)

6-ethyl-bicyclo[2,2,1]-2-heptene

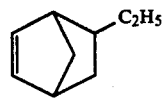

6-ethylidene-bicyclo[2,2,1]-2-heptene (5-ethylidene-2-norbornene)

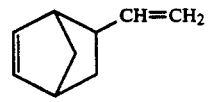

6-phenyl-bicyclo[2,2,1]-hepto-2-ene

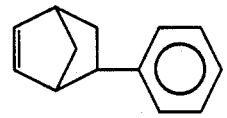

tricyclo[4,3,0,1$^{2.5}$]-3-decene

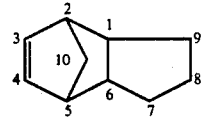

tricyclo[4,3,0,1$^{2.5}$]-3,8-decene (3,8-dihydro-dicyclopentadiene)

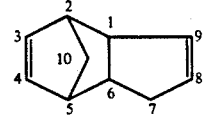

tricyclo[4,4,0,1$^{2.5}$]-3-undecene

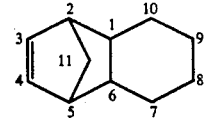

pentacyclo[4,7,0,1$^{2.5}$,0,0$^{8.13}$,1$^{9.12}$]-3-pentadecene

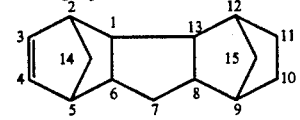

5,10-dimethyl-tetracyclo[4,4,0,1$^{2.5}$,1$^{7.10}$]-3-dodecene

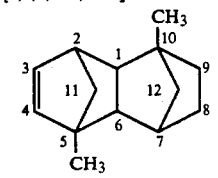

tetracyclo[4,4,0,1$^{2.5}$,1$^{7.10}$]-3-dodecene

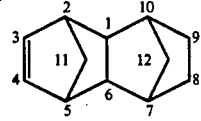

11,12-dimethyl-hexacyclo[6,6,1,1$^{3.6}$,1$^{10.13}$,0$^{2.7}$,0$^{9.14}$]-4-heptadecene

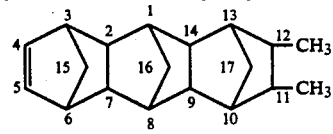

pentacyclo[6,5,1,1$^{3.6}$,0$^{2.7}$,0$^{9.13}$]-4-pentadecene

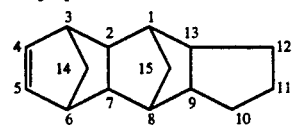

8-ethylidene-9-ethyltetracyclo[4,4,0,1$^{2.5}$,1$^{7.10}$]-3-dodecene

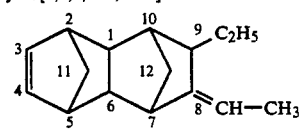

bis(acryloxycarboxy)tricyclo[4,3,0,1$^{2.5}$]-decene

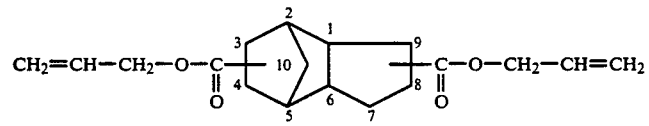

bis(methacryloxy)tricyclo[4,3,0,1$^{2.5}$]-decene

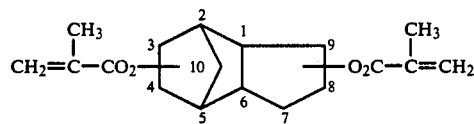

bis(acryloxy)tricyclo[4,3,0,1$^{2.5}$]-decene

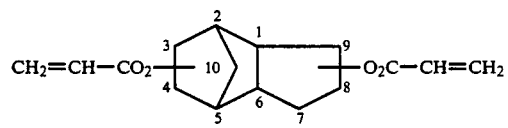

In the cyclic resin of the present invention, at least one member selected from the group consisting of cyclic olefin compounds and bridged polycyclic hydrocarbon compounds is used as a polymeric component and in addition, lower olefins, aromatic compounds or vinyl monomers of lower olefins having 2 to 6 carbon atoms or aromatic compounds capable of being copolymerizable with these polymeric components can be incorporated as a copolymeric component. Examples of the copolymeric component are ethylene, propylene, isoprene, butadiene, methylpentene, norbornene, butene, vinyltoluene and the like. These other copolymeric components can be used individually or in combination.

Polymerization of the cyclic resin of the present invention can be carried out in known manner, as disclosed in Japanese Patent Publication Nos. 11818/1972, 43412/1983, 1442/1986 and 19761/1987, and Japanese Patent Laid-Open Publication Nos. 75700/1975, 129434/1980, 127728/1983, 168708/1985, 115916/1986, 271308/1986, 22118/1988, 22118/1988, 243103/1988 and 180976/1990.

Specifically, the following three methods can be utilized:

(1) Method comprising subjecting a cyclopentadiene and a corresponding olefin or cyclic olefin to additional cyclization reaction (Diels-Alder reaction) to obtain a bridged cyclic hydrocarbon monomer, polymerizing the resulting monomer in a solvent using aluminum, tungsten, vanadium or boron compound as a catalyst to obtain a resinous product and purifying the resinous product to obtain a bridged cyclic hydrocarbon resin.

(2) Method comprising subjecting a monomer corresponding to the polymeric component of the cyclic resin of the present invention, for example, lower alkylcycloalkene compounds, cycloalkadiene compounds, bridged polycyclic alkadiene compounds, bridged polycyclic alkene compounds, etc. to polymerization reaction in a solvent using an aluminum, vanadium, tungsten or boron compound as a catalyst to obtain a high molecular weight resinous product and then subjecting the resinous product to hydrogenation using a platinum catalyst to obtain a cyclic resin of the present invention.

(3) Method comprising polymerizing an acryloyl derivative of a bridged polycyclic compound by light and/or an organic peroxide to obtain a bridged cyclic resin and then purifying the resin to obtain the cyclic resin of the present invention.

In the foregoing three polymerization reactions, furthermore, monomers such as olefin compounds or aromatic compounds can be added to form copolymers. In any of the above described polymerization methods, the presence of monomers as the polymeric components, low molecular weight oligomers, metallic catalysts, etc. in the cyclic resin of the present invention causes generation of odors and degradation of the sanitary properties. This is unfavorable.

Therefore, as the cyclic resin of the present invention, there is preferably used a resin capable of satisfying a softening point of at least 90° C. (JIS K 2207, 2531, ring and ball method) and a bromine number of at most 5 (JIS K 2543). If the bromine number of the cyclic resin exceeds 5, coloration or discoloration will take place in a sanitary rubber article after laminated with the cyclic resin. In order to prevent the coloration or discoloration, an antioxidant is added.

Examples of the antioxidant to be added to the cyclic resin of the present invention are 2-6-di-t-butyl-4-methylphenol(BHT), octadecycl-3-(4'-hydroxy-3',5'-di-t-butylphenyl) propionate (commercial name: Irganox 1076, made by Chiba Geigy Co.), tetrakis[methylene(3,5-d-t-butyl-4-hydroxyphenyl) propionate]-methane (commercial name: Irganox 1010, made by Chiba Geigy Co.), tocophenol, 4,4'-thiobis(6-t-butyl-3-methylphenol) (commercial name: Antage RC, made by Kawaguchi Kagaku K K), bis(2,2,6,6,-tetramethyl-piperidyl) sebacate (commercial name: Sanol LS-770, made by Sankyo K K), 1,3,8-triaza-7,7,9,,9-tetramethyl-n-octyl-spiro[4,5]decane-2,4-dione (commercial name: Sanol LS-772, made by Sankyo K K), etc. These antioxidants function to prevent the cyclic resin from gelling by heat, light or oxygen. Preferably, the antioxidants are added in a proportion of 0.1 to 1 part by weight.

The content of the cyclic olefin monomer in the cyclic resin of the present invention is preferably at least 30% by weight. The cyclic resin has a molecular weight of 5,000 to 100,000,000. The low molecular weight resin is a highly viscous material and the high molecular weight resin is a powdered material. Thus, when laminating or working of the cyclic resin on a rubber body is difficult, it is preferable to use a working assistant. As the working assistant, at least one of higher fatty acids, higher fatty acid esters, silicone oils, fluorinated oils and the like can be added in a proportion of 0 to 5% by weight.

Lamination of a rubber surface with the cyclic resin of the present invention can be carried out by a method comprising dissolving the cyclic resin in a commonly used solvent, i.e. aliphatic or aromatic hydrocarbon solvents or mixtures thereof such as n-hexane, cyclohexane, butane, pentane, cyclooctane, heptane, ethylbenzene, propylbenzne and the like in a proportion of 1 to 8% by weight, applying or spreading the solution to or on a rubber surface, or a method comprising forming the cyclic resin of the present invention in a film by a known technique, e.g. T-die method, elongation method, inflation method, etc. and then laminating the resulting film onto a rubber surface.

In addition, the cyclic resin of the present invention can be mixed with an olefinic resin and laminated on a rubber surface. In this case, at most 10% by weight of a low to middle molecular weight polyethylene or polybutene can be used to improve the workability.

Since the cyclic resin of the present invention has a higher softening point and higher stability to heat, oxygen, oxidation, etc. as well as sanitary property, a method can be employed comprising forming the cyclic resin into a film of 0.1 to 1 mm in thickness, superimposing the film on a non-vulcanized rubber and then conducting simultaneously vulcanization and shaping of the rubber and lamination of the film, which method is economically preferable. As such a method, for example, there are a method described in Japanese Patent Publication No. 5046/1984 and a method comprising laminating a rubber stopper with a plurality of resin films, as disclosed in Japanese Patent Publication No. 53184/1982, the inventors have proposed.

Furthermore, the cyclic resin of the present invention can be applied to a rubber surface of a rubber stopper used for a plastic container, as disclosed in Japanese Patent Laid-Open Publication No. 1275/1990 and Japanese Patent Application No. 399/1990.

A laminated rubber article obtained by laminating a rubber body with the cyclic resin of the present invention in the form of a film can pass the standards provided in "44 Test Method of Plastic Container for Liquid Transfusion" and "43 Test Method of Rubber Stopper for Liquid Transfusion" of JP 11. It is found that a film of the cyclic resin of the present invention has very excellent resistance to water absorption, moisture absorption and moisture permeation.

As the rubber to be laminated with the cyclic resin of the present invention, there can be used commonly used rubbers such as natural rubber, IR (polylsoprene rubber), IIR (isopreneisobutylene rubber), BR (polybutadiene rubber), EPDM (ethylenepropylene-diene rubber), CR (chloroprene rubber), NBR (acrylonitrile-butadiene rubber), and the like, since the cyclic resin is capable of strongly bonding to the rubber surface and wrapping it even in the form of a very thin film and compounding agents in the rubber, e.g. vulcanizing agents, vulcanization accelerators, reinforcing agents do not come out of it, that is, the insaniatry substances contained in the rubber are not subject to elution and contamination of exterior contacted materials therewith, such as foods or pharmaceutical chemicals.

Furthermore, the cyclic resin of the present invention becomes a film with flexibility and elasticity and thus maintain the flexibility and elasticity comparable to a rubber to be laminated therewith.

The following examples are given in order to illustrate the present invention in detail without limiting the same.

SYNTHETIC EXAMPLE OF RESIN OF PRESENT INVENTION

Synthetic Example 1 (DCP Resin Polymer)

1800 ml of purified and dehydrated toluene and 600 g of dehydrated and purified DCP were charged in a three neck flask of 5000 ml, equipped with a stirrer, in a nitrogen atmosphere, to which 140 g of triethylaluminum [Al(C$_2$H$_5$)$_3$], 365 g of triethylamine [N(C$_2$H$_5$)$_3$] and 46 g of titanium tetrachloride (TiCl$_4$) (based on dry weight), as catalysts, were added in order in a nitrogen atmosphere, followed by stirring and polymerizing at 25° C. for 6 hours. After the polymerization, the product was added to 2000 ml of acetoneisopropyl alcohol (1:1) mixed solvent, to which 10 ml of hydrochloric acid was added to precipitate a resin, and the precipitated resin was washed with the above described mixed solvent, thus obtaining 360 g of DCP ring-opened polymer.

1 kg of a cyclohexane solution of 10% by weight of the above described ring-opened polymer and 5 g of Raney nickel were charged in an autoclave of 2000 ml, equipped with a stirrer, the temperature inside the reactor being raised to 120° C., and the mixture was subjected to hydrogenation reaction at a hydrogen pressure of 70 atm for 8 hours. The reaction product was subjected to centrifugal separation and filtration to remove the catalyst contained therein and precipitated in 1000 ml of a mixed solvent of acetone-isopropyl alcohol (1:1) to obtain 100 g of a resin (a) having a softening point of 136° C. and average molecular weight of about 30,000 and being soluble in n-hexane by 5%.

To 100 parts by weight of the thus obtained resin (a) was added 0.3 part by weight of an antioxidant, Irganox 101. Using n-hexane as a solubilizing solvent, the resin (a) was shaped in a film while adding 1.5 parts by weight of dimethylsiloxane and 1.5 part by weight of stearic acid sorbitan ester thereto.

Synthetic Example 2 (DCP-Ethylene Copolymer)

A stirrer and dropping funnel were fitted to the center of a three neck flask of 5000 ml, being dried. 2500 ml of dehydrated toluene and 150 g of dehydrated DCP were charged in the flask, to which 31 g of ethylaluminum sesquichloride and 4.2 g of dichloroethoxyoxovanadium were added as catalysts and through which mixed gases of dry ethylene gas and nitrogen gas ($\frac{1}{2}$) was passed for 7 minutes and passed at 20° C. for 60 minutes. The polymerization was conducted for 30 minutes. 30 ml of methanol was added thereto to stop the copolymerization to precipitate a resinous material, washed with acetone and dried at about 60° C. to obtain 88 g of a copolymer. This copolymer had a DCP content of 68 mol %.

500 g of a cyclohexane solution of 10% by weight of the resulting copolymer resin and 5 g of palladium carbon were charged in an autoclave of 1000 ml, equipped with a stirrer, and after the inside of the autoclave was rinsed with hydrogen, the temperature was raised to 120° C. At the same temperature, the hydrogen pressure was raised to 70 atm and hydrogenation was carried out for 8 hours while supplementing hydrogen at the same pressure. The reaction product was subjected to centrifugal separation and filtration to remove the catalyst contained therein and precipitated in a large amount of mixed solvents of acetone-isopropyl alcohol (1:1) to obtain 60 g of a resin (b) having a softening point of 136° C. and a bromine number of 0.3.

The thus obtained copolymerized resin (b) was formed in a film after adding 3% by weight of stearic acid sorbitan ester, 1% by weight of dimethylpolysiloxane and 0.5% by weight of BHT thereto. In the case of brushing or spraying, it was applied to a rubber surface in the form of a cyclohexane solution (5% by weight).

Synthetic Example 3 (Terpolymer of DCP)

80 g of purified DCP and 10 g of purified isoprene were charged in an autoclave equipped with a stirrer, gradually heated with agitation in a nitrogen atmosphere and polymerized at a temperature of 250° C. for 7 hours. After cooling, the reaction mixture was distilled to remove low temperature volatile fractions at about 120° to 200° C. and subjected to evacuation at 100° to 70° C. to remove volatile materials.

The polymerized product was charged in an autoclave, to which 80 g of cyclohexane and 2 g of Raney nickel were added, and the mixture was subjected to hydrogenation at a hydrogen pressure of 100 kg/cm$^2$ and a temperature of 200° C. for 4 hours. After cooling, the reaction product was filtered to remove the catalyst and distilled to remove the solvent. 0.7% by weight of BHT was added thereto. The resulting resin (c) had a bromine number of 1.5, softening point of 122° C. and contained n-hexane insolubles.

Synthetic Example 4 (Bridged Polycyclic Compound Polymer)

250 g of 8-methyloxycarbonyltetracyclo[4,4,0,1$^{7,10}$]-3-dodecene,

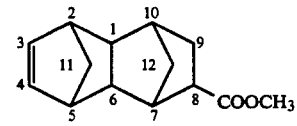

1000 ml of 1,2-dichloroethane and 1.9 g of 1-hexene were charged in a reactor equipped with a stirrer, rinsed with nitrogen gas, to which 46 ml of a chlorobenzene solution of tungsten hexachloride with a concentration of 0.05 mol/liter and 19 ml of a toluene solution of triisobutylaluminum with a concentration of 0.5 mol/liter were added as catalysts, followed by carrying out polymerization reaction at 60° C. for 10 hours. Methanol was added to the polymerized product to stop the polymerization, the solvent was evaporated and the product was washed with an acetone-methanol solution and dried.

The polymerized product was dissolved in 4500 ml of tetrahydrofuran, mixed with 23 g of a palladium-alumina catalyst containing 5% by weight of palladium and then subjected to hydrogenation at a hydrogen pressure of 100 kg/cm$^2$ and a temperature of 170° C. for 5 hours. Then, the similar procedure to Example 1 was repeated to obtain a polymerized resin. 0.5 part by weight of BHT was added thereto to obtain a resin (d) having a bromine number of 0.05 and a softening point of 112° C.

Synthetic Example 5 (Bridged Polycyclic Binary Copolymer)

1000 ml of dried and purified cyclohexane was charged in a reactor of 2000 ml, equipped with a stirrer, to which 30 g of 8,9-dimethyl-tetracyclo-[4,4,0,1$^{2,5}$,1$^{7,10}$]-3-dodecene (synthesized by subjecting cyclopentadiene and dimethylnorbornene to addition and cyclization reaction),

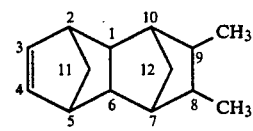

was added under flow of nitrogen gas, and then, 12 g of ethylaluminum sesquichloride [Al($C_2H_5$)$_{1.5}$Cl$_{1.5}$] and 2 g of dichloroethoxyoxovanadium [VO($C_2H_5$)Cl$_2$] were dropwise added. 15 liter of mixed gases of dry ethylene gas and nitrogen gas ($\frac{1}{2}$) were bubbled therein at a temperature of 10° C. for 30 minutes to effect copolymerization reaction. 12 ml of methanol was added to stop the copolymerization reaction and the product was washed with acetone and dried in vacuum.

0.3% by weight of Irganox 1010 was added to the thus obtained copolymer (yield: 28 g; bromine number: 0.5; softening point: 118° C.) to give a resin (e).

Synthetic Example 6 (Bridged Polycyclic terpolymer)

1000 ml of dried and purified toluene was charged in a reactor of 2000 ml, equipped with a stirrer, to which 30.4 g of tetracyclo-[4,4,0,1$^{2.5}$,1$^{7.10}$]-3-dodecene and 3.8 g of 4-methylcyclohexene were added under flow of nitrogen gas, and then, 3.6 g of ethylaluminum sesquichloride and 2.2 g of vanadium oxytrichloride were added. 13 liters of mixed gases of dry ethylene gas and nitrogen gas ($\frac{1}{2}$) were bubbled therein at a temperature of 10° C. for 30 minutes from a has feed pipe to effect polymerization reaction. 20 ml of methanol was added thereto to stop the reaction to obtain 32 g of a polymer having a bromine number of 0.3 and a softening point of 124° C.

0.3% by weight of Irganox 1076 was added to the thus obtained polymer to give a resin (f).

Synthetic Example 7 (Bridged Polycyclic Compound Polymer)

100 g of bis(methacryloxy)tricyclo[4,3,0,1$^{2.5}$]-3-decane and 100 g of cyclohexane were added to a flask, 2 g of benzoyl peroxide was added thereto while flowing nitrogen gas, and the reaction mixture was uniformly mixed, gradually heated and subjected to polymerization reaction at 120° C. The solvent was removed and after adding 4 g of t-butylperoxybenzoate and 1 g of 4,4-thiobis-(6-t-butyl-3-methylphenol), the polymer was used in the form of a 2 wt % solution of cyclohexane. The resulting resin (g) had a softening point of 112° C. and a bromine number of 3.3.

Synthetic Example 8

To 100 parts by weight of the copolymerized resin (g) obtained in Example 7 were added 3 parts by weight of a microwax with a softening point of 80° C. and 3 parts by weight of a low molecular weight ethylene, mixed in a brabender plastomill at a temperature of 120° to 130° C. and the mixture was formed in a film. This mixed resin was referred to as resin (h).

Examples 1 to 8 and Comparative Example 1

Using the resins (a) to (g) obtained in Synthetic Examples 1 to 8, rubber stopper bases were subjected to lamination therewith, the rubber bases being prepared from BR rubber according to the following formulation:

| | |
|---|---|
| BR (Nipol BR 1242 S -commercial name-, made by Nippon Zeon KK, cis content 37.2%, ML$_{1+4}$ 100° C. 53) | 100 parts by weight |
| Powdered Polyethylene (made by Seitetsu Kagaku KK) | 3 |
| Titanium Oxide (made by Ishihara Sangyo KK) | 15 |
| Calcined Clay (Burgess Pigment Co.) | 20 |
| 2,5-dimethyl-2,5-di(t-butylperoxy)hexane | 1 |
| vinyltris($\beta$-methoxy)silane | 1 |

The BR rubber compounding operations and vulcanization operations were carried out according to SRIS (Nippon Gomu Kyokai Kikaku-Japan Rubber Institute Standards-) 3603. The vulcanization condition was 160° C.×12 minutes. The molded rubber article, having a shape of a rubber base 1, as shown in FIG. 1, was immersed in n-hexane solutions of the resins (a) to (g) of the present invention two or more times, coated with a film with a thickness of 0.1 mm and completely dried at a temperature of about 90° C., thus forming a film shown in FIG. 1 on the rubber surface (Examples 1 to 8).

The thus resulting samples and a comparative sample consisting of only the rubber base free from the resin (Comparative Example 1) were subjected to the sanitary test according to "43 Test Method of Rubber Stopper for Liquid Transfusion" of JP 11 to obtain results as shown in Table 1.

Figure 2:
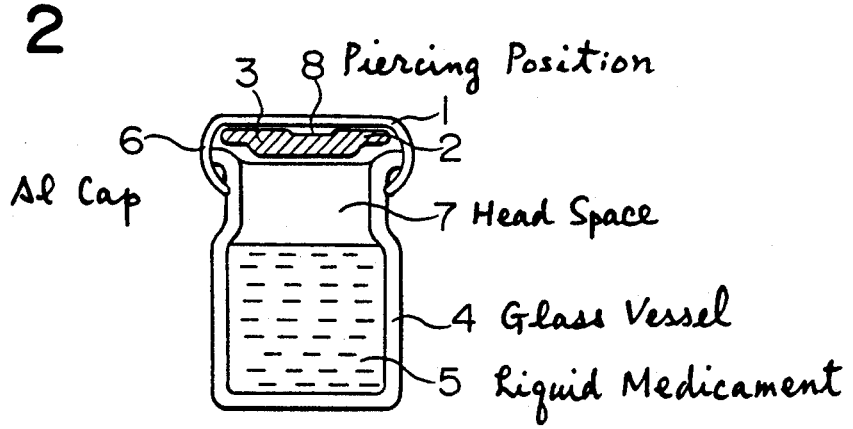
FIG. 2 is a sectional view of another embodiment of the rubber article of the present invention, enclosed in a glass bottle charged with a medical liquor and fastened by an aluminum cap.

These rubber stoppers were applied to a glass container filled with a liquid medicament as shown in FIG. 2, fastened by an aluminum cap and subjected to the special sanitary test, thus obtaining results shown in Table 2.

TABLE 1

| | Test Results of JP 11 | | | | | | | | | |
|---|---|---|---|---|---|---|---|---|---|---|
| | Examples | | | | | | | | Comparative Example 1 | JP 11 Standard |
| | 1 | 2 | 3 | 4 | 5 | 6 | 7 | 8 | | |
| Laminated Resin | a | b | c | d | e | f | g | h | no | |
| Lead | <0.05 | <0.05 | <0.05 | <0.05 | <0.05 | <0.05 | <0.05 | <0.05 | <0.1 | |
| Cadmium | <0.05 | <0.05 | <0.05 | <0.05 | <0.05 | <0.05 | <0.05 | <0.05 | <0.1 | |
| Transmissivity | 99.5 | 99.5 | 99.5 | 99.5 | 99.5 | 99.5 | 99.5 | 99.5 | 98 | >99% |
| Foaming | 0.5 | 0.5 | 0.5 | 0.5 | 0.5 | 0.5 | 0.5 | 0.5 | 1 | <3 minutes |
| pH | 0.4 | 0.3 | 0.4 | 0.5 | 0.5 | 0.4 | 0.3 | 0.5 | 1.2 | difference <1 |
| Cl Salt (ppm) | <0.5 | 0.4 | 0.3 | 0.4 | 0.4 | 0.4 | 0.4 | 0.3 | 2.0 | |
| SO$_4$ Salt (ppm) | <0.5 | <0.5 | <0.5 | <0.5 | <0.5 | <0.5 | <0.5 | <0.5 | — | |
| PO$_3$ Salt (ppm) | <0.3 | <0.3 | <0.3 | <0.3 | <0.3 | <0.3 | <0.3 | <0.3 | — | |
| NH$_4$ Salt (ppm) | <1 | <1 | <1 | <1 | <1 | <1 | <1 | <1 | 2.5 | |
| KMnO$_4$ Reducing Substance (ml) | 0.6 | 0.5 | 0.8 | 0.6 | 0.7 | 0.8 | 1.0 | 0.9 | 1.5 | <2.0 ml |
| Residue on Evaporation (mg) | 0.2 | 0.3 | 0.1 | 0.2 | 0.3 | 0.2 | 0.3 | 0.3 | — | <2.0 mg |
| UV Absorption Spectrum | 0.05 | 0.08 | 0.02 | 0.05 | 0.03 | 0.06 | 0.06 | 0.03 | 0.13 | <0.2 |
| Acute Systemic Toxicity | normal | normal | normal | normal | normal | normal | normal | normal | — | normal |
| Subcutaneous Reaction | normal | normal | normal | normal | normal | normal | normal | normal | — | normal |
| Pyrogen Test | OK | OK | OK | OK | OK | OK | OK | OK | — | OK |
| Hemolysis Test | no | no | no | no | no | no | no | no | — | no |
| Implantation | normal | normal | normal | normal | normal | normal | normal | normal | — | normal |

TABLE 1-continued

Test Results of JP 11

|  | Examples | | | | | | | | Comparative Example 1 | JP 11 Standard |
|---|---|---|---|---|---|---|---|---|---|---|
|  | 1 | 2 | 3 | 4 | 5 | 6 | 7 | 8 | | |
| Property | | | | | | | | | | |

TABLE 2

Test Results of Special Sanitary Test Results

|  | Examples | | | | | | | | Comparative Example 1 | Results |
|---|---|---|---|---|---|---|---|---|---|---|
|  | 1 | 2 | 3 | 4 | 5 | 6 | 7 | 8 | | |
| Laminated Resin | a | b | c | d | e | f | g | h | no | |
| Particulate Matter Counting Test ($\geq 5$ μm) | 1 | 0 | 1 | 2 | 1 | 0 | 1 | 2 | 8 | |
| Rubber Fragments | 0 | 0 | 0 | 0 | 0 | 0 | 0 | 1 | 3 | BS: at most 3 fragments |
| gas in Head Space | little | little | little | little | little | little | little | little | medium | |
| Alkali Resistance | 99.5 | 99.5 | 99.5 | 99.5 | 99.5 | 99.5 | 99.5 | 99.5 | 98 | at least 95% |
| Water Absorption | 0.05 | 0.05 | 0.1 | 0.1 | 0.05 | 0.05 | 0.05 | 0.05 | 0.2 | at most 2% |
| Slidability Unit: Angle | 37 | 38 | 36 | 37 | 36 | 36 | 37 | 36 | 46 | |

The details of the tests shown in Table 1 and 2 are illustrated below:

JP 11 Test

Property of Elution Test, Foaming, pH, Zn, KMnO₄ Reducing Property, Evaporation Residue, UV (ultraviolet ray) Absorption Spectrum A sample is mixed with water in an amount of 10 times as much as the sample and then heated and extracted with high pressure steam at 121° C. for 1 hour. In view of that DIN or BS is carried out by heating at 121° C. for 30 minutes, it is apparent that the extraction condition of JP 11 is the severest.

Acute Toxicity, Subcutaneous Reactions, Feverish Materials, Hemolytic Materials and Transplantation Tests:

These tests are carried out according to JP 11, which are somewhat different from those of DIN, BS or USP.

DIN Test

Detection Test of Metallic Elements (Pb, Cd)

30% HNO₃ is added to 10.0 ml of the test solution obtained in an analogous manner to the elution test of JP 11 to 20 ml and subjected to measurement of the metallic elements by an atomic absorption spectrophotometric method using acetylene. Pb is measured by a hollow vacuum lamp 283.3 μm and Cd is similarly measured.

Other Special Sanitary Test

Particulate Matter Counting Test (Test of Number of Grains from Rubber Stopper)

10 rubber stoppers are charged in a hard glass bottle, to which 300 ml of dust-free water is added, and the mouth of the bottle is wrapped with a film and vibrated by hand at about 2 revolutions per second for 20 seconds. Allowing to stand for 1 hour, the number of fine grains in the water was measured by means of an automatic fine grain meter of light-shielding type (made by HIAC Co.). The presence of fine grains with a grain size of at least 5 μm in an injection liquor is an important item because of causing a problem of clogging blood vessel, etc.

Fragmentation of Rubber

A vial of 10 ml, having a shape shown in FIG. 2 as a designation 4, is charged with 5 ml of water, closed by a rubber stopper 1 and then fastened by an aluminum cap 6. An injection cylinder fitted with a test needle [22 G (0.70×32 mm)] is charged with water and then pierced through a piercing position 8 20 times. At the 20th penetration, the water in the injection cylinder is injected into the vial and the needle is then withdrawn. After vibrating the vial, the rubber stopper is removed, the content liquid is filtered and the number of rubber fragments on the filter paper is counted. This test method is an improved method of BS. BS provides that the number of rubber fragments be at most 3, but in this field, it has lately been desired that it should be at most 2.

Gas Component Test in Head Space

A vial 4 of FIG. 2 is charged with 8 ml of a 2 wt % aqueous solution of NaCl, enclosed by a rubber stopper 3 and fastened by an aluminum cap 6. This glass vial is steam-heated at 121°±1° C. for 60 minutes in a pressure vessel and then allowed to stand for about 10 hours. 5 ml of a sample gas is taken from a head space 7 of the vial using a syringe for gases and then subjected to analysis by a gas chromatography under conditions of column 10% OV-101 (180–200 mesh WHP), carrier gas He 50 ml/min and column temperature 100°–200° C. (raised at 4° C./min), thus checking the presence or height of peaks. This is a test for checking generation of gases in very small amounts from the rubber and additives to be blended, which has lately been considered important.

Alkaline Solution Resistance Test 10 rubber stoppers are charged in an alkali resistance vessel, to which a 0.5 wt % solution of sodium carbonate is added in a proportion of 10 times as much as the weight of the rubber stoppers, and the vessel is enclosed by the rubber stopper and fastened by an aluminum cap. This assembly is then steam-heated at 121° C. for 30 minutes in a high pressure vessel, allowed to stand to room temperature and cooled, followed by removing the rubber stopper. The test solution is taken and subjected to measurement of transmission of a visible part with a wavelength of 430 to 650 nm using a quartz cell. A transmission of at least 95% is regarded as satisfactory. This test is a fundamental test for examining the relationship between the rubber and a medical liquid and a rubber article having a low percent permeability cannot pass this test.

Water Absorption Test

A vulcanized and shaped rubber article is dried at 105° C. at normal pressure for 3 hours, allowed to stand in a desiccator containing a drying agent for about 1 hour and the weight thereof (A) is then precisely measured. Then, the rubber stopper is immersed in purified water in an amount of 10 times as much as the rubber stopper and steam-heated, as it is, at 121°±1° C. for 30 minutes in a pressure vessel. After cooling, only the rubber stopper is allowed to stand for 30 minutes in a desiccator to remove the water on the surface, at which the weight (B) thereof is measured. Thus, {[(B)−(A)/(A)]×100} (%) is calculated and a value of at most 2% by weight is regarded as passing this test.

Slidable Property Test

A rubber stopper is placed on a fluoro resin plate, and while one end of the plate is fixed, the other end thereof is raised at a constant rate to move the rubber stopper. The angle of the plate, at which the rubber stopper starts to move, is measured.

As shown in Table 1, the rubber stoppers laminated with the cyclic resin film of the present invention (Examples 1 to 5) satisfy the standards of JP 11 and are also more excellent in the special sanitary tests as shown in Table 2.

On the other hand, the lamination-free rubber stopper of Comparative Example has some items not satisfying the standards, as shown in Tables 1 and 2. Since PE, PP, PET and fluoro resins are not soluble in solvents (e.g. n-hexane), no thin resin film can be formed from these resins in the form of solutions.

Examples 9 to 13 and Comparative Examples 2 to 4 (Sanitary Tests of Resin-Laminated Slidable Stopper for Syringe)

Figure 4:
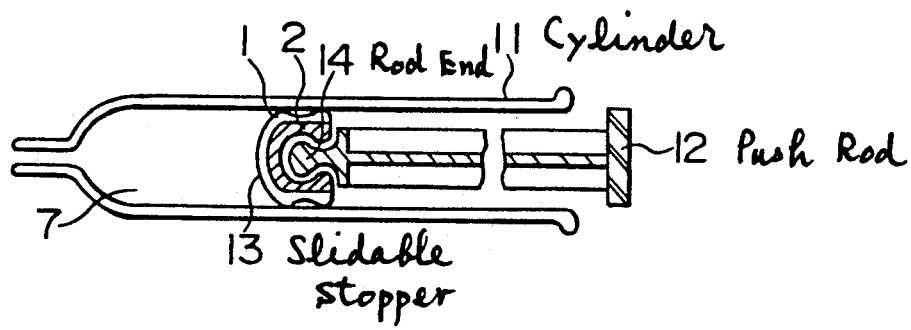
FIG. 4 is a sectional view of a slidable stopper fitted to an end of a push rod of a syringe, the stopper being laminated with a cyclic resin film of the present invention.
Figure 5:
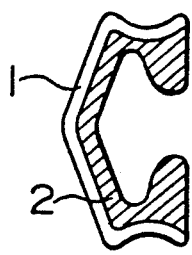
FIG. 5 is a sectional view of a slidable stopper laminated with a cyclic resin film of the present invention.

The cyclic resin of the present invention was compressed by two rolls or a press at a temperature of 100° to 140° C. to form a film of 0.3 to 0.4 mm in thickness. Formation of a slidable laminated rubber stopper was carried out by a method comprising laminating a rubber with the resin film of the present invention simultaneously with vulcanization and shaping of the rubber, specifically using a lower metal mold having a hollow part corresponding to the stopper and an upper metal mold having an end protrusion of a push rod. First, the resin film of the present invention was placed on the surface of the lower metal mold, on which the foregoing compounded rubber of BR was placed in the form of a sheet, and then the upper metal mold was superimposed thereon, followed by compressing at a temperature of 160° C. and about 80 kg/cm², thus obtaining a resin film-laminated slidable stopper (FIG. 4 and FIG. 5).

Laminated slidable stoppers (comparative articles) were obtained in the similar manner to described above using the same metal molds and the same compounded rubber of BR as described above and using films of PE, PP and fluoro resin (referred to as F).

The thus obtained laminated stoppers of the present invention and for comparison were subjected to assessment of the degree of difficulty in bonding the film to the rubber, the elongation of the film and the state of the film subjected to steam sterilization. The results are shown in Table 3.

TABLE 3

|  | Examples | | | | | Comparative Examples | | |
| --- | --- | --- | --- | --- | --- | --- | --- | --- |
|  | 9 | 10 | 11 | 12 | 13 | 2 | 3 | 4 |
| Resin Film | a | b | f | g | h | PE | PP | F |

TABLE 3-continued

|  | Examples | | | | | Comparative Examples | | |
| --- | --- | --- | --- | --- | --- | --- | --- | --- |
|  | 9 | 10 | 11 | 12 | 13 | 2 | 3 | 4 |
| Degree of Difficulty of Film | ⊚ | ⊚ | ⊚ | ⊚ | ⊚ | x | ○ | x |
| Bonding State after Steam Treatment | ⊚ | ⊚ | ⊚ | ⊚ | ⊚ | x | x | ○ |

As shown in Table 3, in the slidable stoppers laminated with the cyclic resin film of the present invention (Examples 9 to 13), the film was strongly bonded to the rubber surface and there was found no breakage nor wrinkles of the film. In the treatment with steam, there were not found poor samples.

On the other hand, PE and F (Comparative Examples 2 and 4) met with breakage of the films during shaping and PP (Comparative Example 3) exhibited good shaping property, but occurrence of water foams in the treatment with steam.

Example 14

Figure 6:
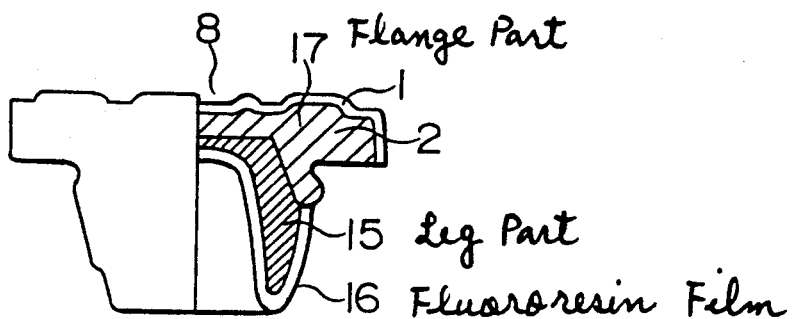
FIG. 6 is a sectional view of a rubber stopper for freeze drying, whose whose leg part is laminated with a fluoro resin and flange part is laminated with a cyclic resin film of the present invention.

In a rubber stopper as shown in FIG. 6, according to the technique described in Japanese Patent Laid-Open Publication No. 272134/1986, firstly, rubber-shaping of a leg part 15 and lamination of a fluoro resin film 16 (surface-treated by sputtering) were simultaneously carried out, and then, rubber-shaping of a flange part 17 and lamination of the cyclic resin film 1 of the present invention were simultaneously carried out.

Figure 7:
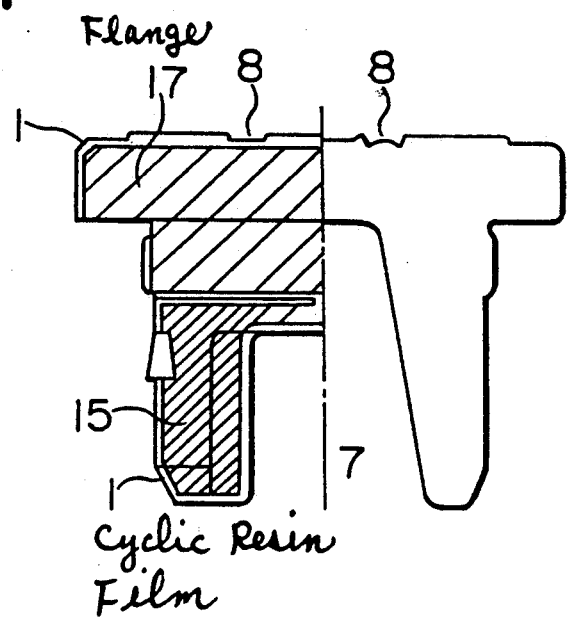
FIG. 7 is a vertically sectional view of a rubber stopper whose leg part in contact with a liquid medicament and flange part are laminated with a cyclic resin film of the present invention.
Figure 8:
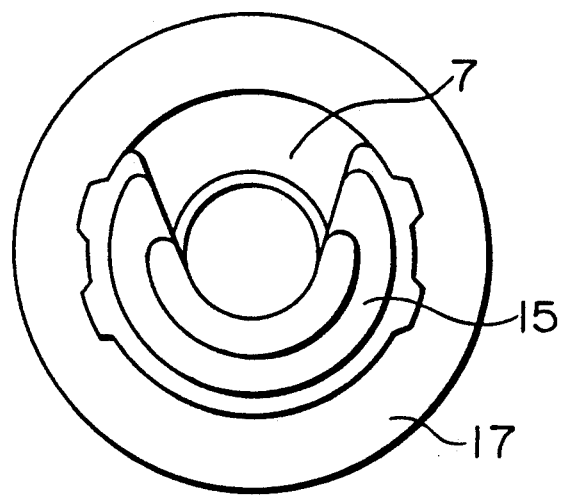
FIG. 8 is a cross-sectional view of the laminated rubber stopper of FIG. 7 (Eglue type rubber stopper).

A rubber stopper as shown in FIGS. 7 and 8 was obtained by laminating both the surfaces of a leg part 15 (in contact with a liquid medicament in a container) and a flange part 17 with the cyclic resin film 1 of the present invention according to the technique described in Japanese Patent Laid-Open Publication No. 272134/1986. When using this rubber stopper for freeze drying of a pharmaceutical chemical in a container, there was no fear of contamination due to rubber fragmentation caused by movement of the rubber stopper.

Example 15

Figure 3:
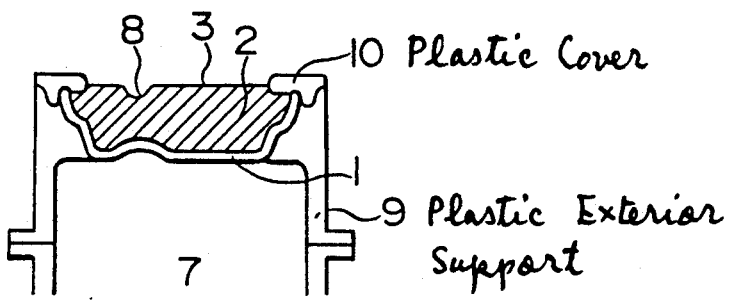
FIG. 3 is a sectional view of a further embodiment of the rubber article of the present invention, enclosed in an exterior support of a plastic container and covered by an upper cover, the laminated part of the rubber article being bonded by fusion with the exterior support and upper cover.

A stopper bonded to a plastic vessel was prepared by laminating a rubber surface to be contacted with a liquid medicament with the cyclic resin film of the present invention, as shown in FIG. 3, according to the technique described in Japanese Patent Laid-Open Publication No. 1275/1990. The feature of the rubber article of this type consists in that a high quality liquid medicament can be given to the human body without contamination of the medicament.

The advantages of the present invention are summarized below:

As illustrated above, the present invention provides a novel sanitary rubber article in which a rubber surface is laminated with the specified cyclic resin according to the present invention and which has the following features:

(a) The cyclic resin body of the present invention is excellent in sanitary property and inert, and is capable of passing the test standards for pharmaceutical chemicals and medical instruments of JP 11. This is also odorless and suitable for foods.

(b) The cyclic resin film of the present invention is readily bonded to a rubber surface and the bonded interface is not easily stripped.

(c) Since a rubber surface is coated with the cyclic resin film of the present invention, the rubber and compounding agents do not contaminate exterior matters, e.g. liquid medicaments.

What is claimed is:

1. A sanitary rubber article having a resin film laminated on the surface of a base resin, said film made from a resin previously produced by polymerizing an aliphatic cyclic olefinic compound or bridged polycyclic hydrocarbon compound, prior to being laminated on the rubber article.

2. The sanitary rubber article as claimed in claim 1, wherein the aliphatic cyclic olefin compound is at least one member selected from the group consisting of monocyclic olefinic compounds and alkyl derivatives and acrylate derivatives thereof.

3. The sanitary rubber article as claimed in claim 1, wherein the bridged polycyclic hydrocarbon compound is one having at least one unsaturated bond in the ring or substituent.

4. The sanitary rubber article as claimed in claim 1, wherein a resin made from the aliphatic cyclic olefinic compound or the bridged polycyclic hydrocarbon compound further comprises a resin produced by polymerizing at least one member selected from the group consisting of lower olefins having 2 to 6 carbon atoms and aromatic vinyl compounds.

5. The sanitary rubber article as claimed in claim 1, wherein a resin made from the aliphatic cyclic olefinic compound or the bridged polycyclic hydrocarbon compound is mixed with an olefin type resin.

6. The sanitary rubber article as claimed in claim 1, wherein a resin made from the aliphatic cyclic olefinic compound or the bridged polycyclic hydrocarbon compound as a polymeric component has a bromine number of at most 5.

7. The sanitary rubber article as claimed in claim 1, wherein a resin made from the aliphatic cyclic olefinic compound or the bridged polycyclic hydrocarbon compound has a softening point of at least 90° C.

* * * * *